(12) United States Patent
Chin et al.

(10) Patent No.: US 7,799,918 B2
(45) Date of Patent: Sep. 21, 2010

(54) ORGANIC METAL COMPLEXES

(75) Inventors: Chih-Lung Chin, Taoyuan County (TW); Wan Chi Chen, Taoyuan County (TW); Kung-Lung Cheng, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 696 days.

(21) Appl. No.: 11/826,338

(22) Filed: Jul. 13, 2007

(65) Prior Publication Data

US 2008/0214818 A1  Sep. 4, 2008

(30) Foreign Application Priority Data

Dec. 28, 2006 (TW) .............................. 95149475 A

(51) Int. Cl.
C07F 15/00 (2006.01)
C09K 11/06 (2006.01)

(52) U.S. Cl. .......................... 546/10; 428/690; 428/917

(58) Field of Classification Search .................. 546/10; 428/690, 917
See application file for complete search history.

(56) References Cited

OTHER PUBLICATIONS

Baldo et al., Applied Physics Letters, vol. 75, No. 1, Jul. 5, 1999, pp. 4-6.
O'Brien et al., Applied Physics Letters, vol. 74, No. 3, Jan. 18, 1999, pp. 442-444.
Tang et al., Appl. Phys. Lett. 51 (12), Sep. 21, 1987, pp. 913-915.
Duan et al., Adv. Mater. 2003, 15, No. 3, Feb. 5, pp. 224-228.
Adachi et al., Applied Physics Letters, vol. 78, No. 11, Mar. 12, 2001, pp. 1622-1624.
Su et al., Adv. Mater. 2003, 15, No. 11, Jun. 5, pp. 884-888.
Tsuboyama et al., J. Am. Chem. Soc. 2003, 125, pp. 12971-12979.

*Primary Examiner*—Charanjit S Aulakh
(74) *Attorney, Agent, or Firm*—Birch, Stewart, Kolasch & Birch, LLP

(57) ABSTRACT

An organic metal complex is provided. The organic metal complex has formula (I):

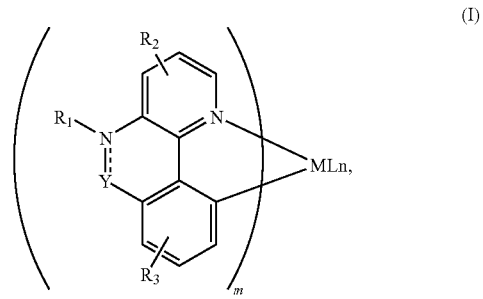

wherein $R_1$ includes hydrogen, C1~C9 alkyl, C5~C8 cycloalkyl, or substituted or non-substituted aromatic groups, $R_2$ and $R_3$ comprise hydrogen, fluorine, trifluoromethyl, C1~C9 alkyl, C5~C8 cycloalkyl, or substituted or non-substituted aromatic groups, Y comprises C—R or carbonyl, wherein R comprises hydrogen, C1~C9 alkyl, C5~C8 cycloalkyl, or substituted or non-substituted aromatic groups, L is a ligand, M comprises iridium, platinum, ruthenium, gold, or palladium, m is 1~3, and n is 0~2, wherein m+n is equal to the valence of M.

16 Claims, No Drawings

ORGANIC METAL COMPLEXES

BACKGROUND OF THE INVENTION

1. Field of the Invention

The invention relates to an organic metal complex, and more specifically to an organic metal complex applied in electroluminescent devices.

2. Description of the Related Art

Since 2000, development of organic light-emitting devices such as OLED has become popular. More than 160 enterprises are invested in OLED researches. The growth of shipping amount exceeds 175% per year. In 2004, the global sales achieved U.S. 4.46 hundred million, increasing 69.6% over the previous year. The OLED industry is continuously developing toward full-color and large-size panels. Display Search predicts, to 2008, the market scale will be increased to U.S. 50 hundred million.

OLED comprises multiple films, capable of luminescence. The C. W. Tang team of Eastman Kodak corporation utilizes $Alq_3$ (tris-(8-hydroxy quinolinol) aluminum) and HTM-2 to prepare an OLED device, published in *Appl. Phys. Lett.* (p 913, 1987). Electrons and holes are confined in an organic layer to increase recombination thereof, achieving low driving voltage and high quantum efficiency. Thus, many corporations are invested in development of various luminescent materials. Additionally, OLED can also applied in, for example, cell phone panel, personal digital assistant (PDA) panel, car panel, computer screen, television screen, and illumination appliance applications due to self-luminescence (without backlight source), low cost, thin profile, high luminescence, no view angle limitation (>165°), high response speed, low driving voltage, and low power consumption.

In a conventional OLED structure, a transparent indium tin oxide (ITO) is formed on a glass substrate or plastic substrate, serving as an anode. A cathode is selected from a low work-function metal such as Mg/Ag or Al/Li. When a voltage is applied, electrons are injected into an emitting layer from the cathode and holes injected into the emitting layer from the anode. After recombination of electrons and holes, the device radiates. The luminescent color of the device is determined by the interior luminescent organic materials.

The luminescent materials are divided into fluorescent materials and phosphorescent materials. According to inter-related research, the complex formed by iridium, two cyclo-metalated ligands, and one negative-charge bidentate ancillary group possesses high luminescent efficiency. The luminescence of the complex can be varied from green to red by alternation of the cyclometalated ligand structures. The complex formed by iridium and three cyclometalated ligands also exhibits high green-light luminescent efficiency. Similarly, the scope of the luminescence can be extended from green to blue by alternation of the cyclometalated ligand structure and modification of number and location of electron-withdrawing groups and electron-donating groups.

In 1999, Forrest provides an organic phosphorescent material, "PtOEP", doped in CBP by evaporation, published in *Appl. Phys. Lett.* 74, 442 (1999). Such devices provide a max external quantum efficiency of 5.6% and a CIE of (0.7, 0.3).

In 2001, Forrest further provides a red phosphorescent material containing iridium, "$Btp_2Ir(acac)$", doped in CBP, published in *Appl. Phys. Lett.* 78, 1622 (2001). Such devices provide a max external quantum efficiency of 7.0%, a max irradiation wavelength of 616 nm, and a CIE of (0.68, 0.32).

In 2003, Conon team provides a series of red phosphorescent materials, published in JACS 125, 12971 (2003). Among these, 1-(phenyl) isoquinoline(piq) is optimal, with a max external quantum efficiency of 10.3%, a max irradiation wavelength of 656 nm, and a CIE of (0.68, 0.32).

In 2003, Prof. Rai-Shung Liu provides a series of phosphorescent materials containing 1-(phenyl) isoquinoline(piq) host, having an irradiation wavelength within 595~630 nm, published in *Adv. Mater.*, 15, 884 (2003). The luminescent color is altered by addition of fluorine to 1-(phenyl) isoquinoline(piq), without deterioration of luminescent efficiency. Among these, $Ir(piq)_2(acac)$ and $Ir(piq-F)_2(acac)$ are optimal, with external quantum efficiency of 8.46% and 8.67% and CIE of (0.68, 0.32) and (0.61, 0.36) under 20 $mA/cm^2$.

In 2003, Prof. Chien-Hong Cheng provides a reddish orange phosphorescent material containing dibenzo[f,h]quinoxaline serving as a ligand, "$Ir(DBQ)_2(acac)$" and "$Ir(MDQ)_2(acac)$", published in *Adv. Mater.*, 15, 224 (2003), with external quantum efficiency of 11.9% and 12.4% and CIE of (0.62, 0.38) and (0.60, 0.39), respectively.

In 2005, SANYO provides $Q_3Ir$ and $(QR)_2Ir(acac)$ containing diphenyl quinoxaline as a ligand, with an irradiation wavelength within 653~675 nm. While 600 $cd/m^2$, $Q_3Ir$ has a CIE of (0.70, 0.28) and the conventional high-purity red phosphorescent material, "$Btp_2Ir(acac)$", has a CIE of (0.68, 0.32). Such materials possess high luminescence, high efficiency, high CIE stability, and an absolute quantum efficiency of 50~79%. Additionally, the luminescent time of $Q_3Ir$ is merely 1 μs at exciting state, ⅕ of $Btp_2Ir(acac)$.

Thompson provides a green phosphorescent material, "Ir(ppy)$_3$", doped in CBP, published in *Appl. Phys. Lett.* 75, 4 (1999), with a max external quantum efficiency of 8.0%, a max irradiation wavelength of 510 nm, and a CIE of (0.27, 0.63).

Improvement of OLED luminescent material performance is desirable, for example, material optics, electrochemistry, thermal stability, luminescent efficiency, and cost.

BRIEF SUMMARY OF THE INVENTION

The invention provides an organic metal complex having formula (I):

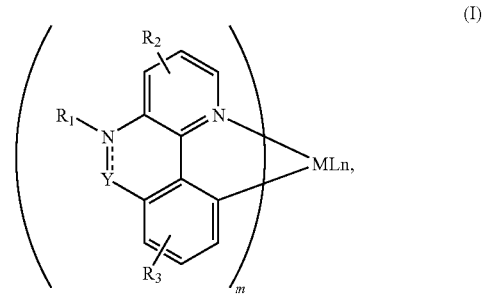

wherein $R_1$ includes hydrogen, C1~C9 alkyl, C5~C8 cycloalkyl, or substituted or non-substituted aromatic groups, $R_2$ and $R_3$ comprise hydrogen, fluorine, trifluoromethyl, C1~C9 alkyl, C5~C8 cycloalkyl, or substituted or non-substituted aromatic groups, Y comprises C—R or carbonyl, wherein R comprises hydrogen, C1~C9 alkyl, C5~C8 cycloalkyl, or substituted or non-substituted aromatic groups, L is a ligand, M comprises iridium, platinum, ruthenium, gold, or palladium, m is 1~3, and n is 0~2, wherein m+n is equal to the valence of M.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides an organic metal complex having formula (I):

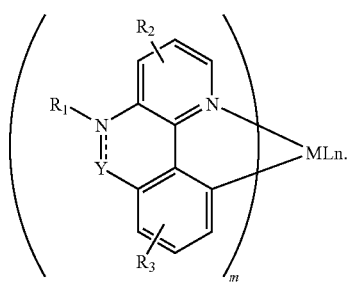
(I)

In formula (I), $R_1$ may comprise hydrogen, C1~C9 alkyl (preferably C1~C6 alkyl, most preferably C1~C4 alkyl), C5~C8 cycloalkyl, or substituted or non-substituted aromatic groups. $R_2$ and $R_3$ may comprise hydrogen, fluorine, trifluoromethyl, C1~C9 alkyl (preferably C1~C6 alkyl, most preferably C1~C4 alkyl), C5~C8 cycloalkyl, or substituted or non-substituted aromatic groups. Y may comprise C—R or carbonyl, wherein R may be hydrogen, C1~C9 alkyl, C5~C8 cycloalkyl, or substituted or non-substituted aromatic groups. L is a ligand. M may comprise iridium, platinum, ruthenium, gold, or palladium. m is 1~3. n is 0~2. m+n is equal to the valence of M.

The aromatic group may comprise heterocyclic rings containing oxygen, sulfur, or nitrogen. L may comprise:

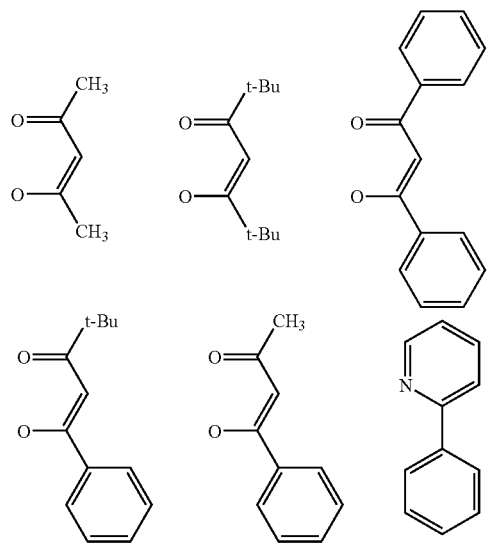

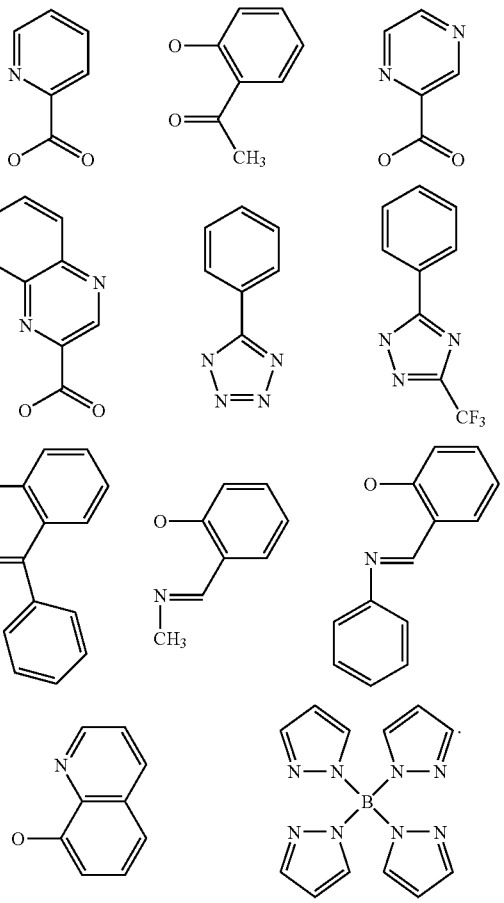

One embodiment of the invention provides an organic metal complex having formula (II):

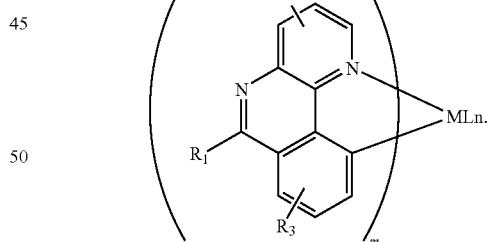
(II)

In formula (II), $R_1$ may comprise hydrogen, C1~C9 alkyl (preferably C1~C6 alkyl, most preferably C1~C4 alkyl), C5~C8 cycloalkyl, or substituted or non-substituted aromatic groups. $R_2$ and $R_3$ may comprise hydrogen, fluorine, trifluoromethyl, C1~C9 alkyl (preferably C1~C6 alkyl, most preferably C1~C4 alkyl), C5~C8 cycloalkyl, or substituted or non-substituted aromatic groups. L is a ligand. M may comprise iridium, platinum, ruthenium, gold, or palladium. m is 1~3. n is 0~2. m+n is equal to the valence of M.

The aromatic group may comprise heterocyclic rings containing oxygen, sulfur, or nitrogen. L may comprise:

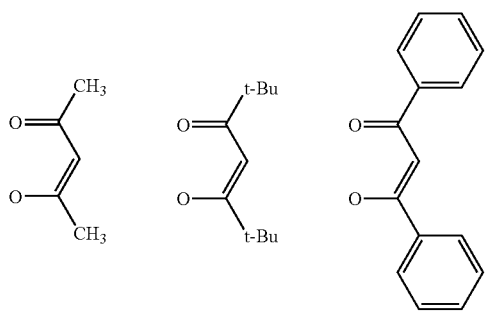
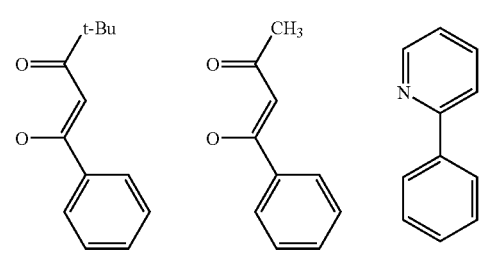
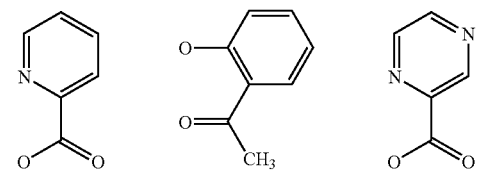
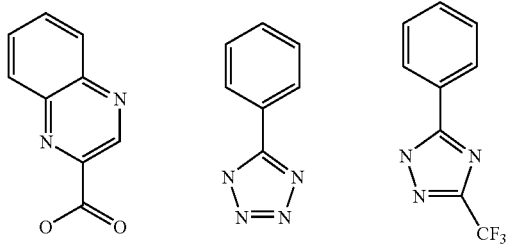
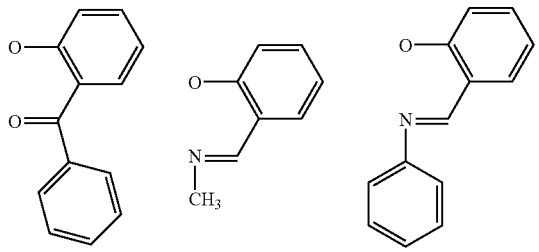
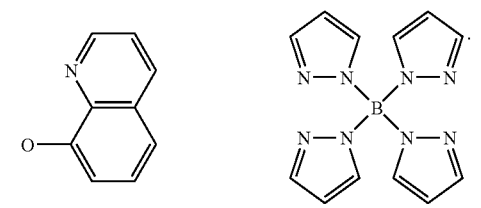

One embodiment of the invention provides an organic metal complex having formula (III):

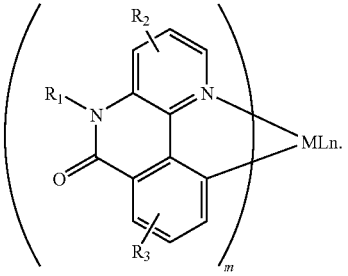

In formula (III), $R_1$ may comprise hydrogen, C1~C9 alkyl (preferably C1~C6 alkyl, most preferably C1~C4 alkyl), C5~C8 cycloalkyl, or substituted or non-substituted aromatic groups. $R_2$ and $R_3$ may comprise hydrogen, fluorine, trifluoromethyl, C1~C9 alkyl (preferably C1~C6 alkyl, most preferably C1~C4 alkyl), C5~C8 cycloalkyl, or substituted or non-substituted aromatic groups. L is a ligand. M may comprise iridium, platinum, ruthenium, gold, or palladium. m is 1~3. n is 0~2. m+n is equal to the valence of M.

The aromatic group may comprise heterocyclic rings containing oxygen, sulfur, or nitrogen. L may comprise:

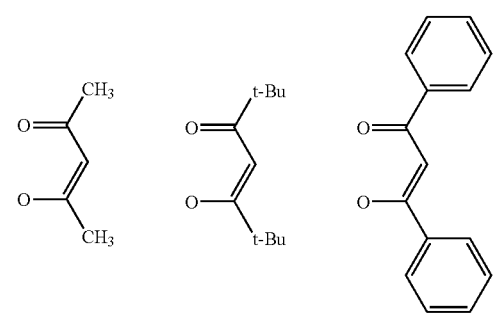
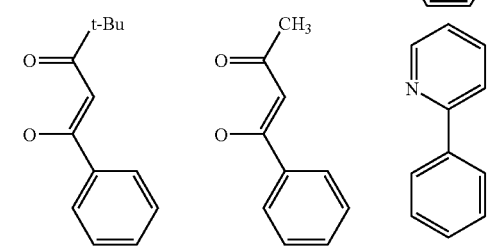
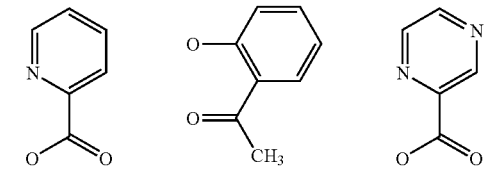
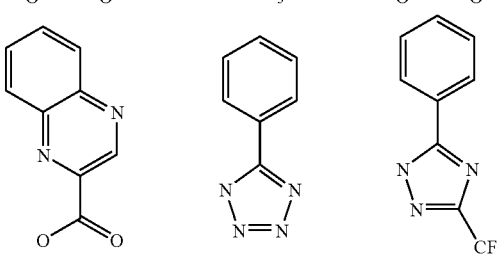

-continued

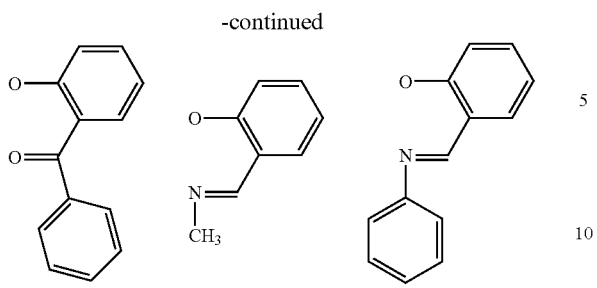

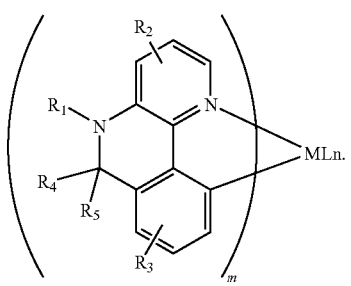

One embodiment of the invention provides an organic metal complex having formula (IV):

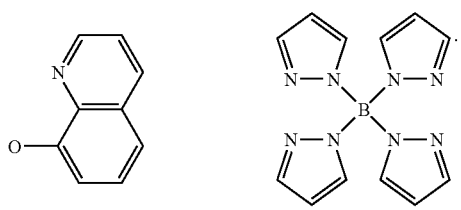

(IV)

In formula (IV), $R_1$, $R_4$, and $R_5$ may comprise hydrogen, C1~C9 alkyl (preferably C1~C6 alkyl, most preferably C1~C4 alkyl), C5~C8 cycloalkyl, or substituted or non-substituted aromatic groups. $R_2$ and $R_3$ may comprise hydrogen, fluorine, trifluoromethyl, C1~C9 alkyl (preferably C1~C6 alkyl, most preferably C1~C4 alkyl), C5~C8 cycloalkyl, or substituted or non-substituted aromatic groups. L is a ligand. M may comprise iridium, platinum, ruthenium, gold, or palladium. m is 1~3. n is 0~2. m+n is equal to the valence of M.

The disclosed organic metal complex is a phosphorescence compound, applied in electroluminescent devices, for example, organic light-emitting devices (OLEDs).

The preparation of the organic metal complex having formula (I) is as follows. A coordination compound such as -continued and a metal halide such as Iridium chloride (IrCl$_3$) were reacted in a solvent such as 2-ethoxyethanol. After filtration, a halogen-bridged dimer complex such as chlorine-bridged dimer complex was formed. The dimer complex was then reacted with another coordination compound such as acetylacetone or picolinic acid in a solvent such as 2-ethoxyethanol to prepare the organic metal complex having formula (I).

EXAMPLE 1

Preparation of benzo[c][1,5]naphthyridine

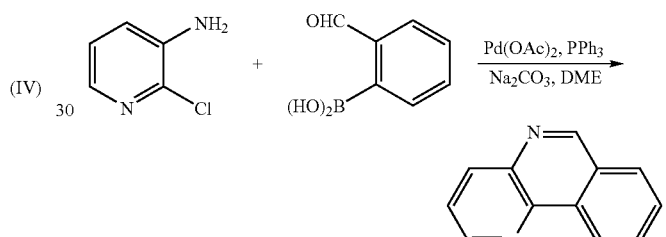

2.3 g 3-amino-2-chloropyridine (20 mmol) was dissolved by 45 mL dimethyl ether (DME) in a round-bottomed flask. 0.24 g palladium acetate (Pd(OAc)$_2$), 0.567 g triphenylphosphine (PPh$_3$), and 27 mL sodium carbonate (Na$_2$CO$_3$) solution were mixed in another flask. After the two flasks were mixed and stirred until a white solid was precipitated, 3.5 g 2-formyl phenyl boronic acid (23.3 mmol) was added and stirred for 24 hr under nitrogen. After extraction by ethyl acetate, drying, concentration, and purification by silicon-gel column, 1.82 g yellow solid was obtained, with a yield of 51%.

$^1$H NMR (CDCl$_3$, 400 MHz) spectrum data

δ9.39 (s, 1H), 9.22 (d, J=8.2 Hz, 1H), 9.06-9.04 (m, 1H), 8.53 (d, J=8.2 Hz, 1H), 8.13 (d, J=7.9 Hz, 1H), 8.00 (d, J=7.5 Hz, 1H), 7.87 (d, J=7.5 Hz, 1H), 7.75-7.72 (m, 1H).

EXAMPLE 2

Preparation of 6-methyl-benzo[c][1,5]naphthyridine

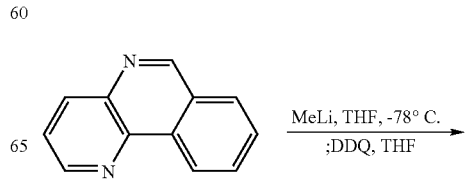

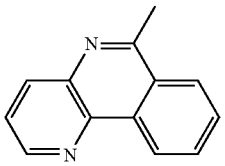

1.0 g benzo[c][1,5]naphthyridine (5.5 mmol) was dissolved in 30 mL tetrahydrofuran (THF) and then cooled to −78° C. under nitrogen with stirring. 4.4 mL methyl lithium (MeLi) (6.6 mmol, 1.5M) was added and reacted for 1 hr. After quenching the reaction by a saturated ammonium chloride (NH$_4$Cl) solution, extraction by ethyl acetate, drying, and concentration, 30 mL THF and 1.87 g 2,3-dichloro-5,6-dicyano-1,4-benzoquinone (DDQ) (8.2 mmol) were added and reacted for 8 hr. After extraction by ethyl acetate, drying, concentration, and purification by silicon-gel column, 0.83 g light yellow solid was obtained, with a yield of 77%.

$^1$H NMR (CDCl$_3$, 400 MHz) spectrum data

δ9.23 (d, J=8.2 Hz, 1H), 8.96 (dd, J=4.3, 1.4 Hz, 1H), 8.37 (dd, J=8.2, 1.4 Hz, 1H), 8.22 (d, J=8.2 Hz, 1H), 7.95 (t, J=7.1 Hz, 1H), 7.84 (t, J=7.1 Hz, 1H), 7.97-7.64 (m, 1H), 3.08 (s, 1H).

EXAMPLE 3

Preparation of 5,6-dimethyl-5,6-dihydro-benzo[c][1,5]naphthyridine

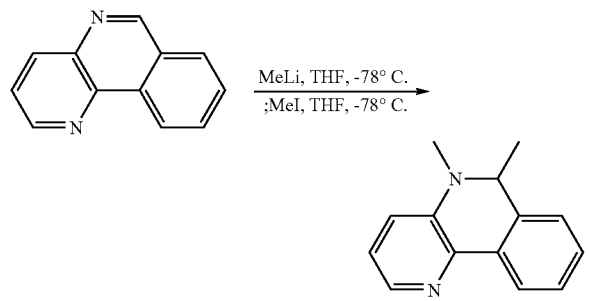

0.55 g benzo[c][1,5]naphthyridine (3.1 mmol) was dissolved in 15 mL tetrahydrofuran (THF) and then cooled to −78° C. under nitrogen with stirring. 2.3 mL methyl lithium (MeLi) (3.4 mmol, 1.5M) was added and reacted for 1 hr. Next, 0.43 g methyl iodide (MeI) (3.7 mmol) was added and reacted for 1 hr at −78° C. After quenching the reaction by a saturated ammonium chloride (NH$_4$Cl) solution, extraction by ethyl acetate, drying, concentration, and purification by silicon-gel column, 0.59 g light yellow solid was obtained, with a yield of 91%.

$^1$H NMR (CDCl$_3$, 400 MHz) spectrum data 8.30 (d, J=7.5 Hz, 1H), 8.00 (d, J=4.6 Hz, 1H), 7.41-7.31 (m, 2H), 7.14-7.08 (m, 2H), 6.91 (d, J=8.2 Hz, 1H), 4.49 (q, J=6.5 Hz, 1H), 2.98 (s, 3H), 1.21 (d, J=6.5 Hz, 3H).

EXAMPLE 4

Preparation of N-(2-chloro-pyridin-3-yl)-benzamide

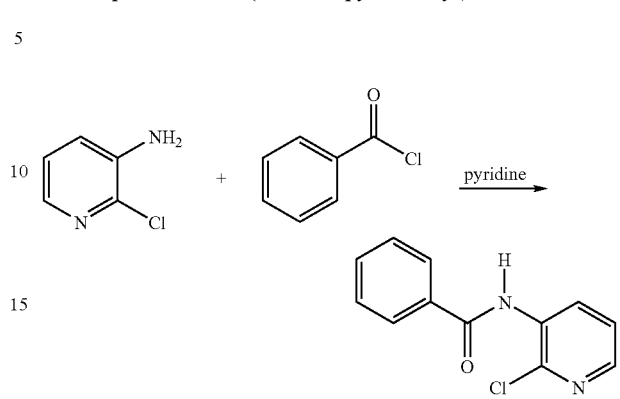

4.57 g 3-amino-2-chloropyridine (36 mmol) and 30 mL pyridine were mixed in an ice bath. 5.0 g benzoyl chloride (36 mol) was then added. After return to room temperature and reaction for 4 hr, the reaction was quenched by water. After extraction three times by ethyl acetate, an ethyl acetate layer was collected and washed by 1M HCl solution. After drying, filtration, concentration, and purification by silicon-gel column, 7.21 g solid was obtained, with a yield of 88%.

$^1$H NMR (CDCl$_3$, 400 MHz) spectrum data

δ8.92-8.89 (m, 1H), 8.21 (brs, 1H), 8.15-8.13 (m, 1H), 7.93-7.90 (m, 2H), 7.61-7.33 (m, 3H), 7.34-7.30 (m, 1H).

EXAMPLE 5

Preparation of N-(2-chloro-pyridin-3-yl)-N-methyl-benzamide

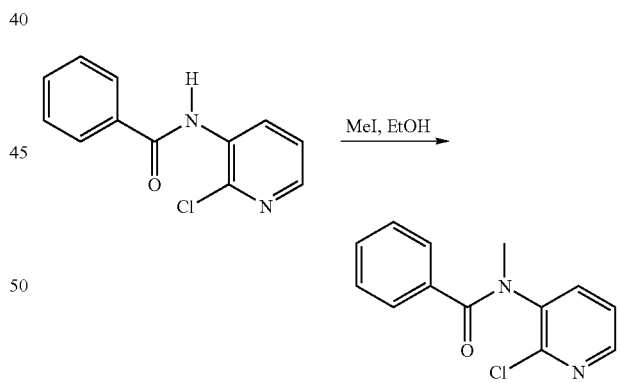

4.6 g N-(2-chloro-pyridin-3-yl)-benzamide (20 mmol), 8.2 g potassium carbonate (K$_2$CO$_3$) (60 mmol), and 50 mL ethanol were added and stirred in a round-bottomed flask. 4.2 g methyl iodide (MeI) (30 mmol) was then added and reacted for 24 hr. After cooling to room temperature, the reaction was quenched by water. After extraction three times by ethyl acetate, removal of water by magnesium sulphate (MgSO$_4$), concentration, and purification by column, 4.18 g white solid was obtained, with a yield of 85%.

$^1$H NMR (CDCl$_3$, 400 MHz) spectrum data

δ8.24 (brs, 1H), 7.40-7.12 (m, 7H), 3.34 (s, 3H).

EXAMPLE 6

Preparation of 5-methyl-5H-benzo[c][1,5]naphthyridin-6-one

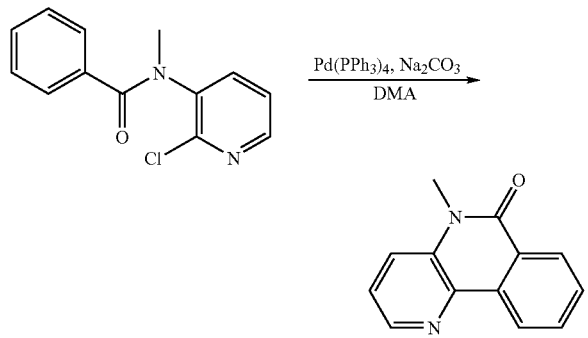

3.94 g N-(2-chloro-pyridin-3-yl)-N-methyl-benzamide (16 mmol), 1.85 g tetrakis(triphenylphosphine) palladium (Pd(PPh$_3$)$_4$) (1.6 mmol), 8.48 g sodium carbonate (Na$_2$CO$_3$) (80 mmol), and 50 mL N,N-dimethyl acetamide (DMA) were added in a flask and reacted for 24 hr under nitrogen. After cooling to room temperature, the reaction was quenched by water. After filtration, concentration, and purification by column, 3.06 light yellow solid was obtained, with a yield of 91%.

$^1$H NMR (CDCl$_3$, 400 MHz) spectrum data
δ8.87 (d, J=7.9 Hz, 1H), 8.63-8.60 (m, 1H), δ8.52 (d, J=7.9 Hz, 1H), 7.87-7.83 (m, 1H), 7.73-7.68 (m, 2H), 7.51-7.46 (m, 1H), 3.81 (s, 3H).

EXAMPLE 7

Preparation of N-(2-chloro-pyridin-3-yl)-N-hexyl-benzamide

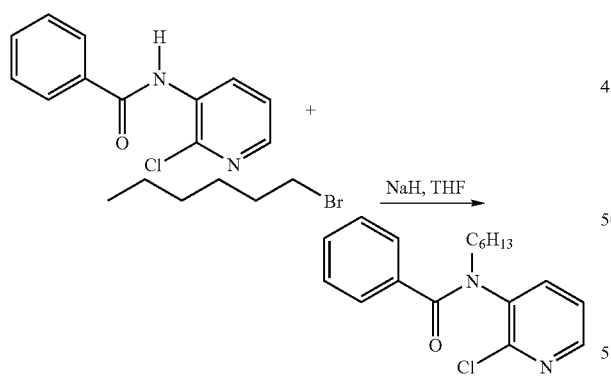

0.63 g sodium hydride (NaH) (26 mmol) and 50 mL tetrahydrofuran (THF) were added in an ice bath with stirring. 3.01 g N-(2-chloro-pyridin-3-yl)-benzamide (13 mmol) and 40 mL THF were then added and reacted for 30 min. Next, 3.28 g 1-bromo-hexane (20 mmol) was added and reacted for 24 hr. After cooling to room temperature, the reaction was quenched by water. After extraction three times by ethyl acetate, removal of water by magnesium sulphate (MgSO$_4$), concentration, and purification by column, 2.39 g white solid was obtained, with a yield of 58%.

$^1$H NMR (CDCl$_3$, 400 MHz) spectrum data
δ8.24 (brs, 1H), 7.36-7.17 (m, 7H), 4.21-3.47 (m, 2H), 1.67-0.87 (m, 11H).

EXAMPLE 8

Preparation of 5-hexyl-5H-benzo[c][1,5]naphthyidin-6-one

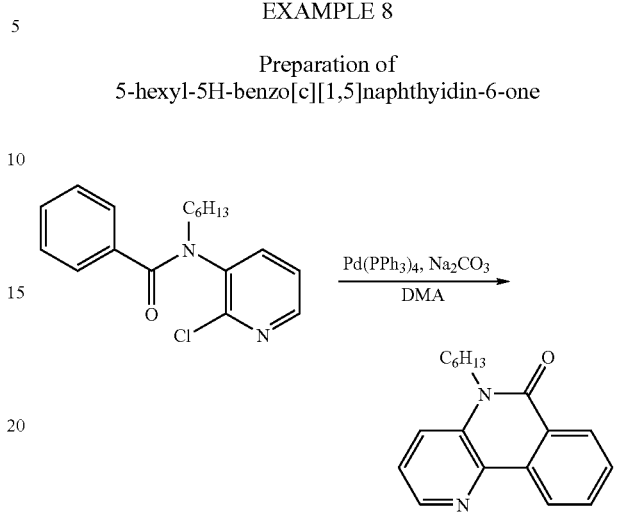

1.8 g N-(2-chloro-pyridin-3-yl)-N-hexyl-benzamide (5.6 mmol), 1.0 g tetrakis(triphenylphosphine) palladium (Pd(PPh$_3$)$_4$) (0.56 mmol), 3.0 g sodium carbonate (Na$_2$CO$_3$) (28 mmol), and 30 mL N,N-dimethyl acetamide (DMA) were added in a flask and reacted for 24 hr under nitrogen. After cooling to room temperature, the reaction was quenched by water. After filtration, concentration, and purification by column, 1.5 light yellow solid was obtained, with a yield of 90%.

$^1$H NMR (CDCl$_3$, 400 MHz) spectrum data
δ8.86 (d, J=8.0 Hz, 1H), 8.60-8.58 (m, 1H), 8.51 (d, J=8.0 Hz, 1H), 7.84-7.81 (m, 1H), 7.72-7.66 (m, 2H), 7.49-7.45 (m, 1H), 4.35 (t, J=7.8 Hz, 2H), 1.80-1.73 (m, 2H), 1.52-1.48 (m, 2H), 1.40-1.32 (m, 4H), 0.91 (t, J=6.8 Hz, 3H).

EXAMPLE 9

Preparation of N-(2-chloro-pyridin-3-yl)-2-trifluoromethyl-benzamide

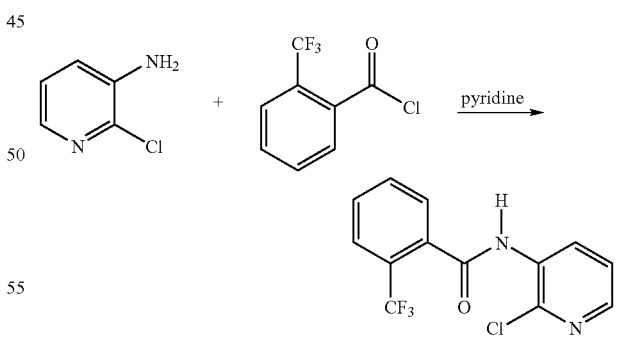

4.57 g 3-amino-2-chloropyridine (36 mmol) and 30 mL pyridine were mixed in an ice bath. 8.24 g 2-trifluoromethyl benzoyl chloride (40 mol) was then added. After return to room temperature and reaction for 4 hr, the reaction was quenched by water. After extraction three times by ethyl acetate, an ethyl acetate layer was collected and washed by 1M HCl solution. After drying, filtration, concentration, and purification by silicon-gel column, 9.9 g solid was obtained, with a yield of 92%.

¹H NMR (CDCl₃, 400 MHz) spectrum data
8.88 (d, J=8.0 Hz, 1H), 8.20 (d, J=4.6 Hz, 1H), 7.97 (s, 1H), 7.81 (d, J=7.5 Hz, 1H), 7.70-7.61 (m, 2H), 7.37-7.33 (m, 1H).

EXAMPLE 10

Preparation of N-(2-chloro-pyridin-3-yl)-N-methyl-2-trifluoromethyl-benzamide

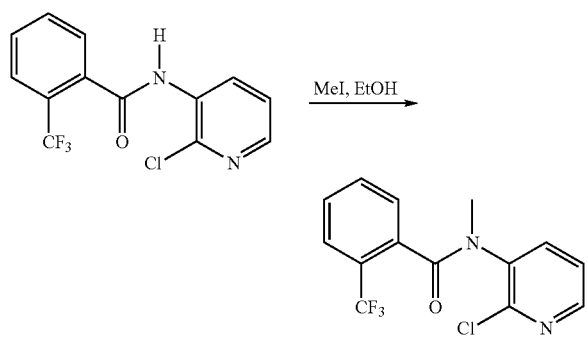

8.0 g N-(2-chloro-pyridin-3-yl)-2-trifluoromethyl-benzamide (26.6 mmol), 1.1 g potassium carbonate (K₂CO₃) (80 mmol), and 100 mL ethanol were added and stirred in a round-bottomed flask. 5.7 g methyl iodide (MeI) (40 mmol) was then added and reacted for 12 hr. After cooling to room temperature, the reaction was quenched by water. After extraction three times by ethyl acetate, removal of water by magnesium sulphate (MgSO₄), concentration, and purification by column, 8.3 g white solid was obtained, with a yield of 88%.

¹H NMR (CDCl₃, 400 MHz) spectrum data
8.21 (dd, J=4.7, 1.7 Hz, 1H), 7.97-7.42 (m, 1H), 7.63-7.52 (m, 2H), 7.45-7.39 (m, 1H), 7.37-7.25 (m, 1H), 7.07 (dd, J=7.7, 4.7 Hz, 1H), 3.39 (s, 1H).

EXAMPLE 11

Preparation of 5-methyl-7-trifluoromethyl-5H-benzo[c][1,5]naphthyridin-6-one

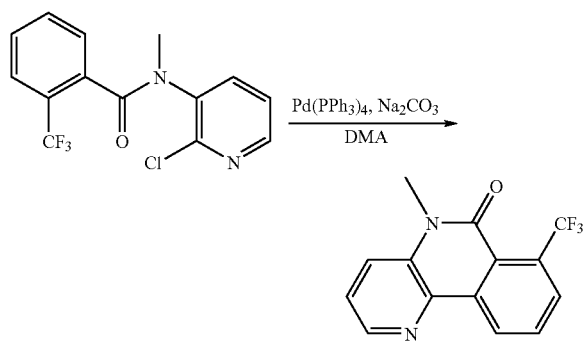

4.5 g N-(2-chloro-pyridin-3-yl)-N-methyl-2-trifluoromethyl-benzamide (14.3 mmol), 2.2 g tetrakis(triphenylphosphine) palladium (Pd(PPh₃)₄) (1.4 mmol), 9.7 g sodium carbonate (Na₂CO₃) (71.5 mmol), and 50 mL N,N-dimethyl acetamide (DMA) were added in a flask and reacted for 18 hr under nitrogen. After cooling to room temperature, the reaction was quenched by water. After filtration, concentration, and purification by column, 3.73 light yellow solid was obtained, with a yield of 94%.

¹H NMR (CDCl₃, 400 MHz) spectrum data
9.23 (d, J=7.9 Hz, 1H), 8.59 (d, J=4.4 Hz, 1H), 8.11 (d, J=7.7 Hz, 1H), 7.88 (dd, J=7.9, 7.7 Hz, 1H), 7.67 (d, J=8.4 Hz, 1H), 7.50 (dd, J=8.4, 4.4 Hz, 1H), 3.80 (s, 3H).

EXAMPLE 12

Preparation of N-(2-chloro-pyridin-3-yl)-2,3-difluoro-benzamide

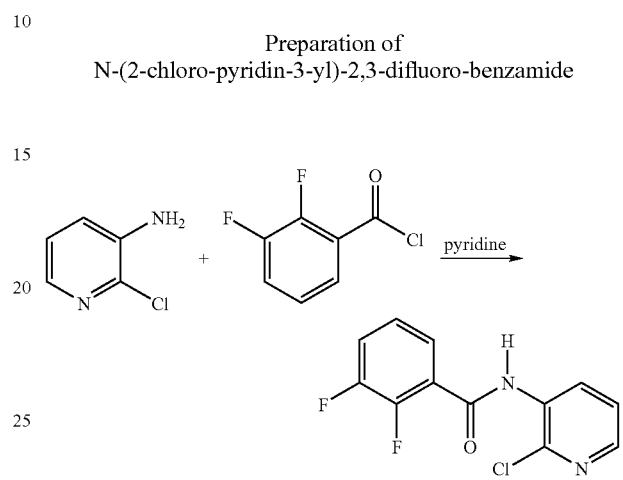

3.31 g 3-amino-2-chloropyridine (25.8 mmol) and 20 mL pyridine were mixed in an ice bath. 5.0 g 2,3-difluoro-benzoyl chloride (28.4 mmol) was then added. After return to room temperature and reaction for 4 hr, the reaction was quenched by water. After extraction three times by ethyl acetate, an ethyl acetate layer was collected and washed by 1M HCl solution. After drying, filtration, concentration, and purification by silicon-gel column, 6.4 g solid was obtained, with a yield of 93%.

¹H NMR (CDCl₃, 400 MHz) spectrum data
9.04 (brs, 1H), 8.90 (dd, J=8.0, 1.0 Hz, 1H), 8.18 (dd, J=4.6, 1.2 Hz, 1H), 7.91 (dd, J=7.8, 6.7 Hz, 1H), 7.43-7.25 (m, 3H).

EXAMPLE 13

Preparation of N-(2-chloro-pyridin-3-yl)-N-methyl-benzamide

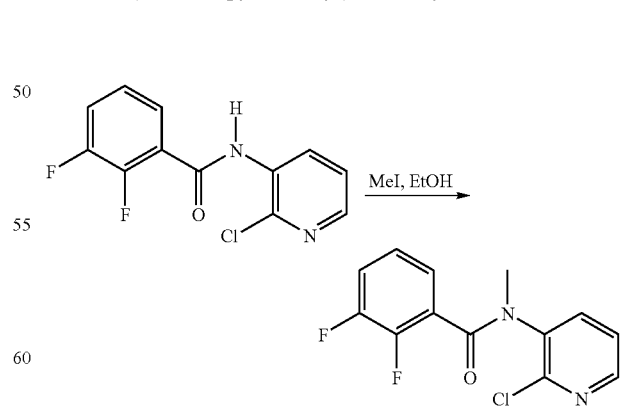

5.0 g N-(2-chloro-pyridin-3-yl)-benzamide (18.6 mmol), 7.7 g potassium carbonate (K₂CO₃) (56 mmol), and 60 mL ethanol were added and stirred in a round-bottomed flask. 3.97 g methyl iodide (MeI) (27.9 mmol) was then added and reacted for 12 hr. After cooling to room temperature, the reaction was quenched by water. After extraction three times by ethyl acetate, removal of water by magnesium sulphate (MgSO$_4$), concentration, and purification by column, 5.05 g white solid was obtained, with a yield of 96%.

$^1$H NMR (CDCl$_3$, 400 MHz) spectrum data 8.27 (dd, J=4.7, 1.6 Hz, 1H), 7.65 (dt, J=7.7, 1.9 Hz, 1H), 7.21 (dd; J=7.7, 4.7 Hz, 1H), 7.17-6.96 (m, 3H), 3.42 (s, 3H).

EXAMPLE 14

Preparation of 7,8-difluoro-5-methyl-5H-benzo[c][1,5]naphthyridin-6-one

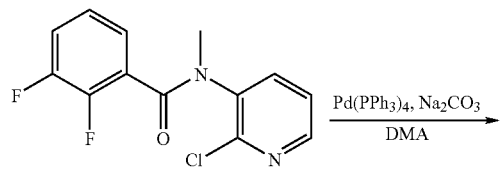

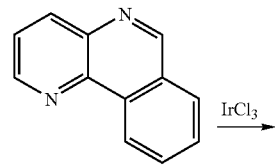

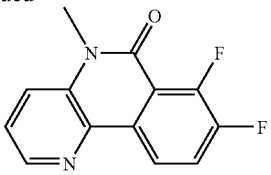

4.5 g N-(2-chloro-pyridin-3-yl)-N-methyl-benzamide (15.9 mmol), 1.85 g tetrakis(triphenylphosphine) palladium (Pd(PPh$_3$)$_4$) (1.6 mmol), 8.4 g sodium carbonate (Na$_2$CO$_3$) (80 mmol), and 40 mL N,N-dimethyl acetamide (DMA) were added in a flask and reacted for 16 hr under nitrogen. After cooling to room temperature, the reaction was quenched by water. After filtration, concentration, and purification by column, 3.99 light yellow solid was obtained, with a yield of 87%.

EXAMPLE 15

Preparation of (BND)$_2$Ir(acac)

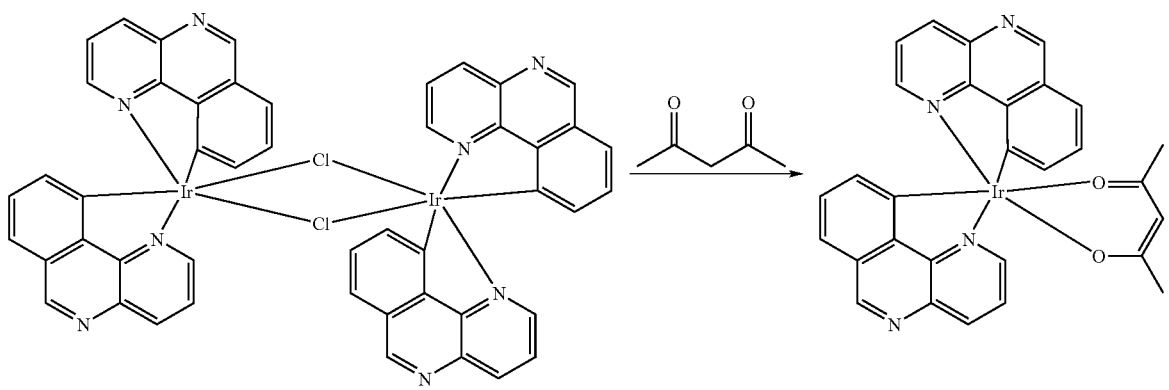

0.6 g Iridium (III) chloride hydrate (2 mmol), 0.93 g benzo[c][1,5]naphthyridine (4.4 mmol), 24 mL 2-ethoxy ethanol, and 7 mL water were added and reacted for 24 hr under nitrogen. After cooling, filtration, and washing by small amount of methanol, a chlorine-bridged dimer complex was obtained. The complex, 1.06 g sodium carbonate (Na$_2$CO$_3$) (10 mmol), 25 mL 2-ethoxyanol, and 0.4 g acetylacetone (4 mmol) were then mixed and reacted for 10 hr under nitrogen. After cooling, solid was precipitated and washed by small amount of water. After purification by silicon-gel column, 0.3 g yellow solid was obtained, with a yield of 41%.

$^1$H NMR (CDCl$_3$, 400 MHz) spectrum data

δ9.19 (s, 2H), 8.85 (d, J=5.2 Hz, 2H), 8.55-8.52 (m, 2H), 7.78-7.73 (m, 2H), 7.46 (d, J=7.7 Hz, 2H), 7.09 (t, J=7.4 Hz, 2H), 6.48-6.45 (m, 2H), 5.33 (s, 1H), 1.83 (s, 6H).

EXAMPLE 16

Preparation of (MBND)₂Ir(acac)

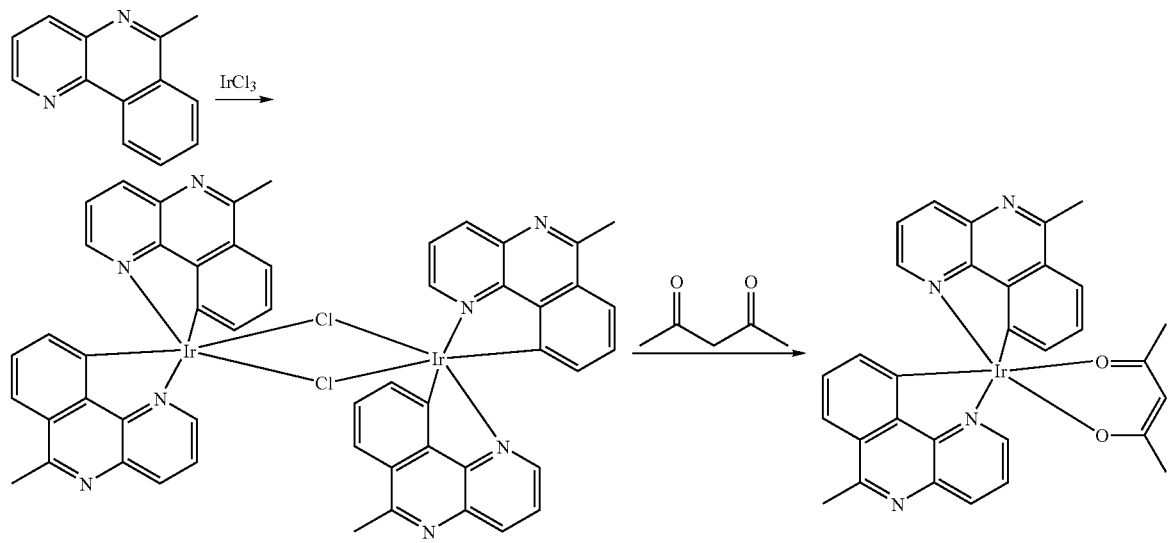

0.3 g Iridium (III) chloride hydrate (1.2 mmol), 0.5 g 6-methyl-benzo[c][1,5]naphthyridine (2.6 mmol), 12 mL 2-ethoxy ethanol, and 4 mL water were added and reacted for 24 hr under nitrogen. After cooling, filtration, and washing by small amount of methanol, a chlorine-bridged dimer complex was obtained. The complex, 0.64 g sodium carbonate (Na₂CO₃) (6 mmol), 15 mL 2-ethoxyanol, and 0.24 g acetylacetone (2.4 mmol) were then mixed and reacted for 8 hr under nitrogen. After cooling, solid was precipitated and washed by small amount of water. After purification by silicon-gel column, 0.49 g yellow solid was obtained, with a yield of 60%.

¹H NMR (CDCl₃, 400 MHz) spectrum data 8.78 (d, J=5.2 Hz, 2H), 8.42 (d, J=8.0 Hz, 2H), 7.72-7.67 (m, 2H), 7.50 (d, J=8.0 Hz, 2H), 7.06 (d, J=7.4 Hz, 2H), 6.43 (t, J=7.2 Hz, 2H), 5.31 (s, 1H), 3.00 (s, 6H), 1.82 (s, 6H).

EXAMPLE 17

Preparation of (DMBND)₂Ir(acac)

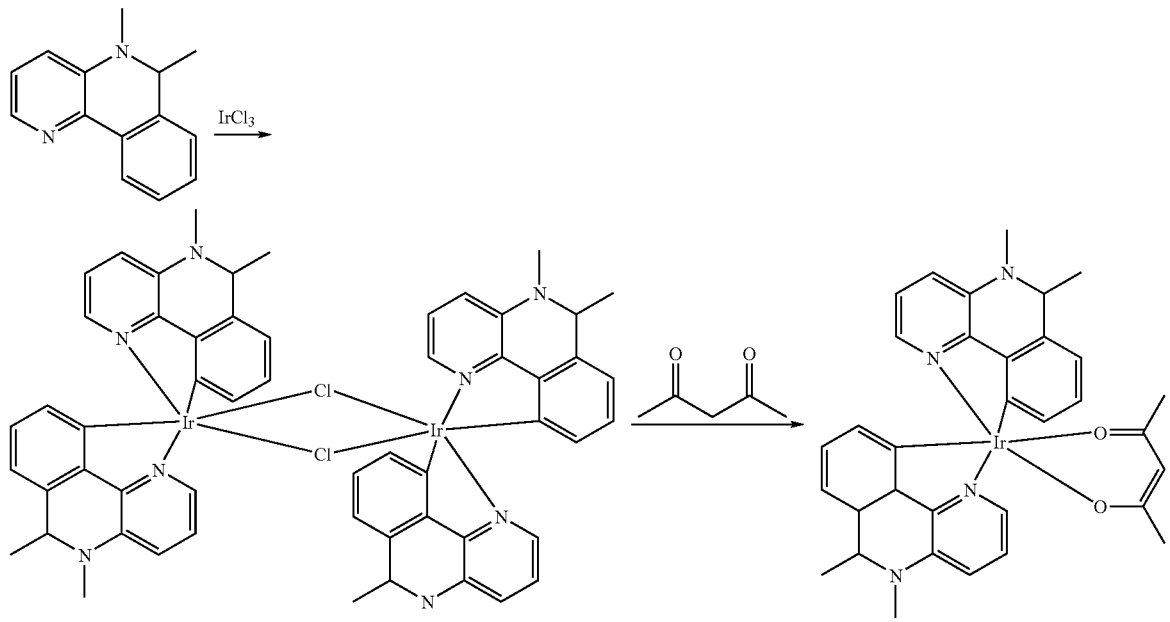

0.32 g Iridium (III) chloride hydrate (1.1 mmol), 0.5 g 5,6-dimethyl-5,6-dihydro-benzo[c][1,5]naphthyridine (2.4 mmol), 9 mL 2-ethoxy ethanol, and 3 mL water were added and reacted for 24 hr under nitrogen. After cooling, filtration, and washing by small amount of methanol, a chlorine-bridged dimer complex was obtained. The complex, 0.58 g sodium carbonate (Na$_2$CO$_3$) (5.5 mmol), 15 mL 2-ethoxy-anol, and 0.11 g acetylacetone (2.2 mmol) were then mixed and reacted for 8 hr under nitrogen. After cooling, solid was precipitated and washed by small amount of water. After purification by silicon-gel column, 0.38 g yellow solid was obtained, with a yield of 49%.

EXAMPLE 18

Preparation of (DMBND)$_2$Ir(pic)

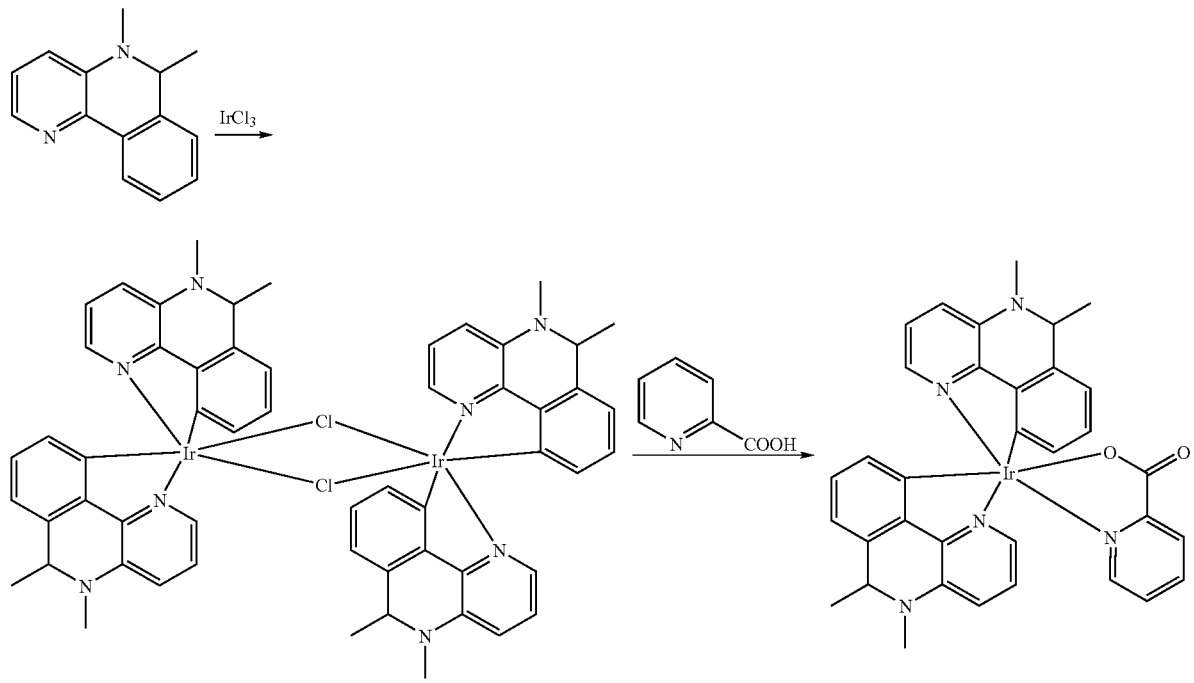

0.32 g Iridium (III) chloride hydrate (1.1 mmol), 0.5 g 5,6-dimethyl-5,6-dihydro-benzo[c][1,5]naphthyridine (2.4 mmol), 9 mL 2-ethoxy ethanol, and 3 mL water were added and reacted for 24 hr under nitrogen. After cooling, filtration, and washing by small amount of methanol, a chlorine-bridged dimer complex was obtained. The complex, 0.58 g sodium carbonate (Na$_2$CO$_3$) (5.5 mmol), 15 mL 2-ethoxy-anol, and 0.31 g picolinic acid (2.2 mmol) were then mixed and reacted for 8 hr under nitrogen. After cooling, solid was precipitated and washed by small amount of water. After purification by silicon-gel column, 0.4 g yellow solid was obtained, with a yield of 51%.

EXAMPLE 19

Preparation of (C1BNO)$_2$Ir(acac)

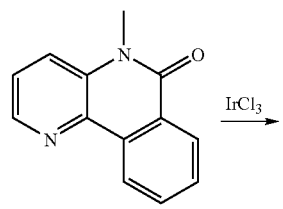

-continued

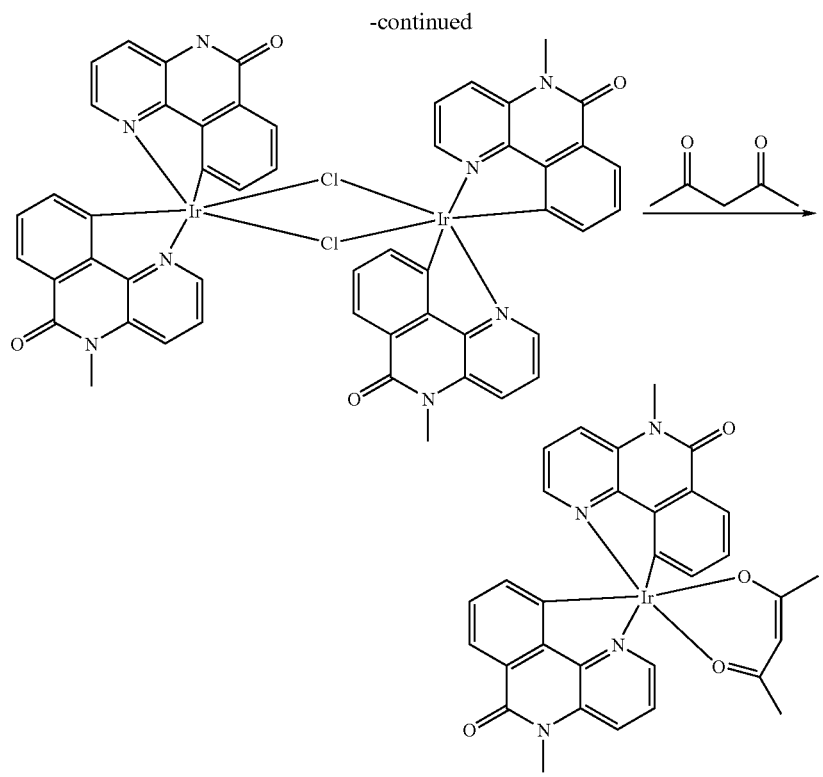

0.6 g Iridium (III) chloride hydrate (2 mmol), 0.79 g 5-methyl-5H-benzo[c][1,5]naphthyridin-6-one (4.4 mmol), 24 mL 2-ethoxy ethanol, and 7 mL water were added and reacted for 24 hr under nitrogen. After cooling, filtration, and washing by small amount of methanol, a chlorine-bridged dimer complex was obtained. The complex, 1.06 g sodium carbonate ($Na_2CO_3$) (10 mmol), 25 mL 2-ethoxyanol, and 0.4 g acetylacetone (4 mmol) were then mixed and reacted for 9 hr under nitrogen. After cooling, solid was precipitated and washed by small amount of water. After purification by silicon-gel column, 0.65 g yellow solid was obtained, with a yield of 46%.

$^1$H NMR ($CDCl_3$, 400 MHz) spectrum data

δ8.41 (d, J=5.3 Hz, 2H), 7.74 (d, J=7.6 Hz, 2H), 7.68 (d, J=8.4 Hz, 2H), 7.47-7.45 (m, 2H), 6.99-6.97 (m, 2H), 6.49-6.46 (m, 2H), 5.30 (s, 1H), 3.83 (s, 6H), 1.57 (s, 6H).

EXAMPLE 20

Preparation of (C1BNO)$_2$Ir(pic)

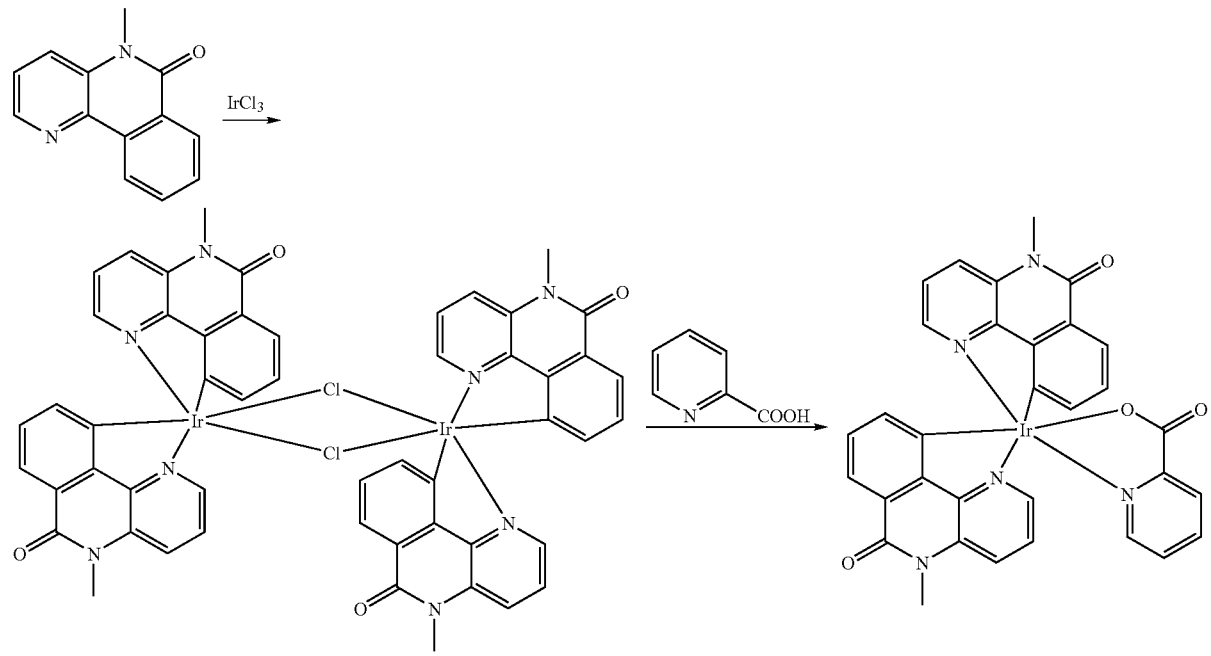

0.6 g Iridium (III) chloride hydrate (2 mmol), 0.79 g 5-methyl-5H-benzo[c][1,5]naphthyridin-6-one (4.4 mmol), 24 mL 2-ethoxy ethanol, and 7 mL water were added and reacted for 24 hr under nitrogen. After cooling, filtration, and washing by small amount of methanol, a chlorine-bridged dimer complex was obtained. The complex, 1.06 g sodium carbonate ($Na_2CO_3$) (10 mmol), 25 mL 2-ethoxyanol, and 0.49 g picolinic acid (4 mmol) were then mixed and reacted for 9 hr under nitrogen. After cooling, solid was precipitated and washed by small amount of water. After purification by silicon-gel column, 0.58 g yellow solid was obtained, with a yield of 40%.

$^1$H NMR (CDCl$_3$, 400 MHz) spectrum data

δ8.67 (d, J=5.2 Hz, 1H), 8.35 (d, J=7.7 Hz, 1H), 7.93 (t, J=7.7 Hz, 1H), 7.87 (d, J=7.5 Hz, 1H), 7.83-7.80 (m, 2H), 7.67 (d, J=8.3 Hz, 2H), 7.47-7.43 (m, 1H), 7.38-7.35 (m, 2H), 7.26-7.22 (m, 1H), 7.14-7.04 (m, 2H), 6.67 (d, J=7.3 Hz, 1H), 6.46 (d, J=7.3 Hz, 1H), 3.81 (s, 3H), 3.80 (s, 3H).

EXAMPLE 21

Preparation of (C1BNO)$_2$Ir(prz)

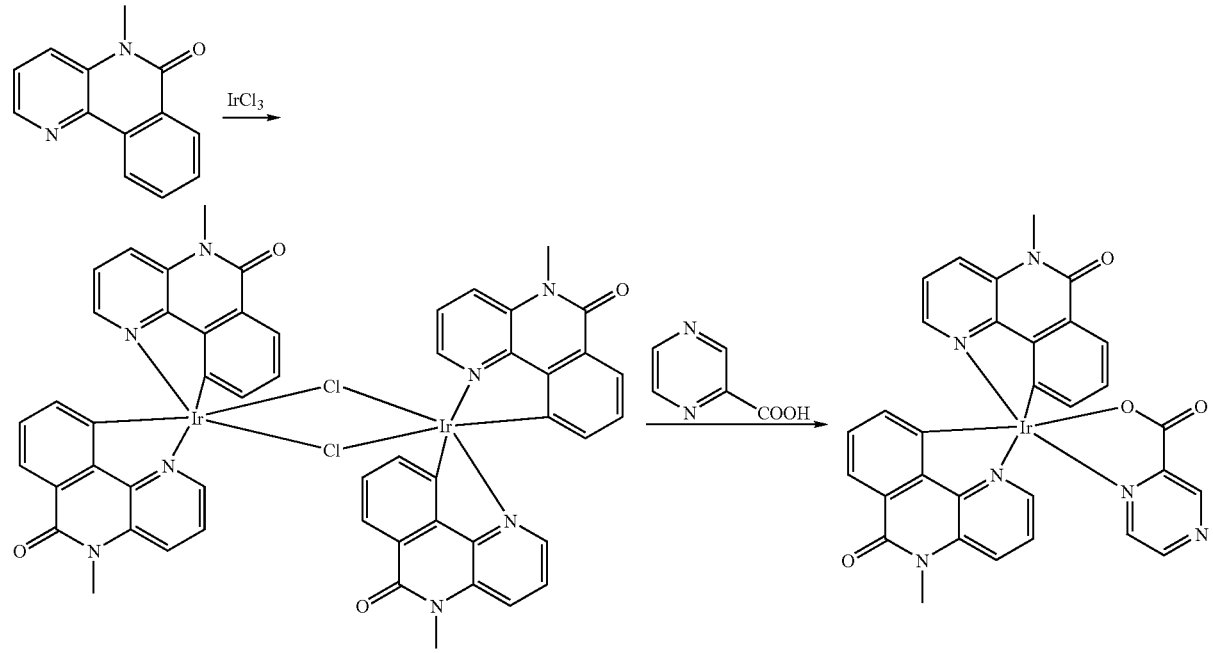

0.6 g Iridium (III) chloride hydrate (2 mmol), 0.79 g 5-methyl-5H-benzo[c][1,5]naphthyridin-6-one (4.4 mmol), 24 mL 2-ethoxy ethanol, and 7 mL water were added and reacted for 24 hr under nitrogen. After cooling, filtration, and washing by small amount of methanol, a chlorine-bridged dimer complex was obtained. The complex, 1.06 g sodium carbonate ($Na_2CO_3$) (10 mmol), 25 mL 2-ethoxyanol, and 0.5 g pyrazine-2-carboxylic acid (4 mmol) were then mixed and reacted for 9 hr under nitrogen. After cooling, solid was precipitated and washed by small amount of water. After purification by silicon-gel column, 0.6 g yellow solid was obtained, with a yield of 41%.

$^1$H NMR (CDCl$_3$, 400 MHz) spectrum data 9.50 (s, 1H), 8.66 (d, J=2.9 Hz, 1H), 8.61 (d, J=5.5 Hz, 1H), 7.87 (d, J=7.7 Hz, 1H), 7.82-7.68 (m, 4H), 7.52-7.47 (m, 1H), 7.36 (d, J=5.5 Hz, 1H), 7.23-7.26 (m, 1H), 7.12 (t, J=7.7 Hz, 1H), 7.07 (t, J=7.7 Hz, 1H), 6.64 (d, J=7.4 Hz, 1H), 6.41 (d, J=7.4 Hz, 1H), 3.80 (s, 3H), 3.77 (s, 3H).

EXAMPLE 22

Preparation of (C1BNO)$_2$Ir(qnx)

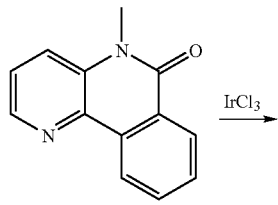

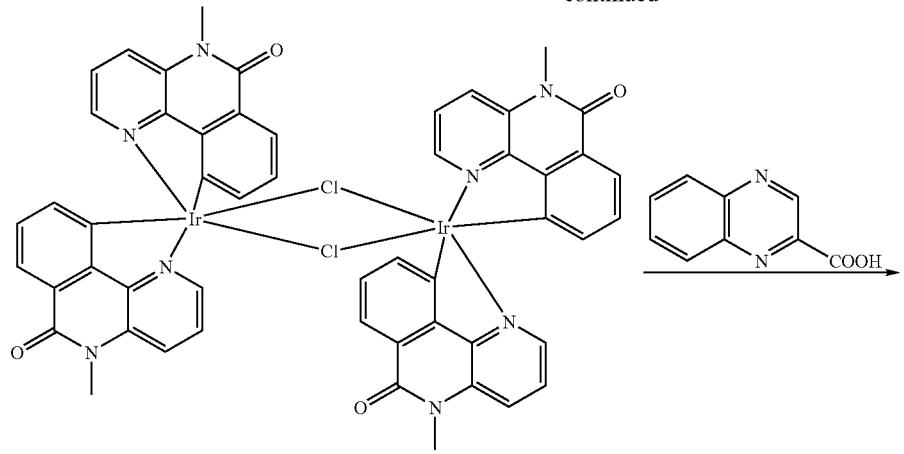

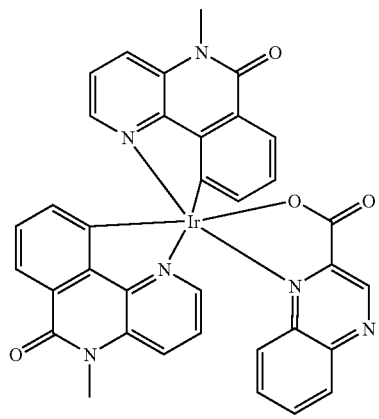

0.6 g Iridium (III) chloride hydrate (2 mmol), 0.79 g 5-methyl-5H-benzo[c][1,5]naphthyridin-6-one (4.4 mmol), 24 mL 2-ethoxy ethanol, and 7 mL water were added and reacted for 24 hr under nitrogen. After cooling, filtration, and washing by small amount of methanol, a chlorine-bridged dimer complex was obtained. The complex, 1.06 g sodium carbonate ($Na_2CO_3$) (10 mmol), 25 mL 2-ethoxyanol, and 0.7 g quinoxaline-2-carboxylic acid (4 mmol) were then mixed and reacted for 9 hr under nitrogen. After cooling, solid was precipitated and washed by small amount of water. After purification by silicon-gel column, 0.63 g yellow solid was obtained, with a yield of 40%.

$^1$H NMR ($CDCl_3$, 400 MHz) spectrum data 9.85 (s, 1H), 8.58 (d, J=5.5 Hz, 1H), 8.20 (d, J=8.4 Hz, 1H), 7.93-7.75 (m, 4H), 7.68 (d, J=8.5 Hz, 1H), 7.64 (d, J=8.5 Hz, 1H), 7.47-7.43 (m, 2H), 7.31-7.15 (m, 3H), 7.05 (t, J=7.6 Hz, 1H), 6.76 (d, J=7.4 Hz, 1H), 6.22 (d, J=7.4 Hz, 1H), 3.80 (s, 3H), 3.77 (s, 3H).

EXAMPLE 23

Preparation of (CF3C1BNO)$_2$Ir(pic)

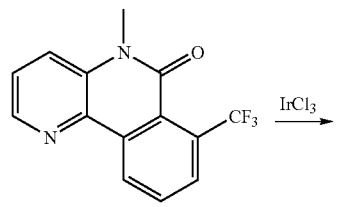

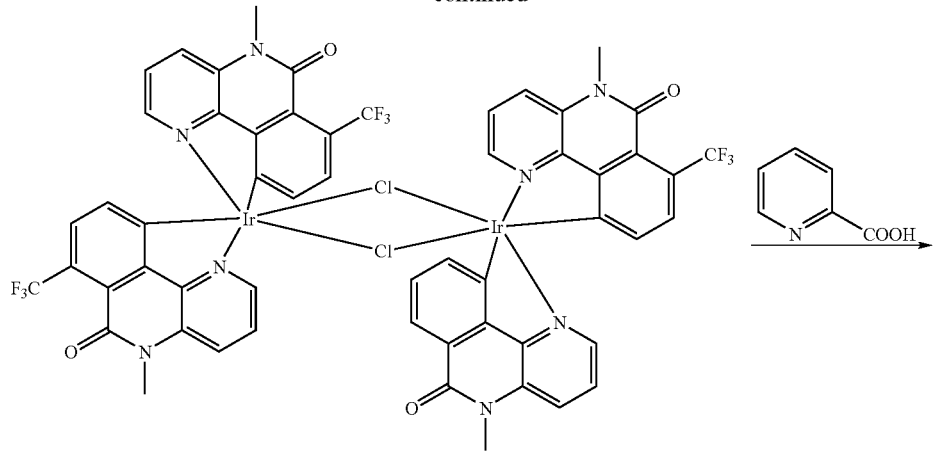

0.88 g Iridium (III) chloride hydrate (2.9 mmol), 1.8 g 5-methyl-7-trifluoromethyl-5H-benzo[c][1,5]naphthyridin-6-one (6.4 mmol), 15 mL 2-ethoxy ethanol, and 5 mL water were added and reacted for 24 hr under nitrogen. After cooling, filtration, and washing by small amount of methanol, a chlorine-bridged dimer complex was obtained. The complex, 1.54 g sodium carbonate ($Na_2CO_3$) (14.5 mmol), 20 mL 2-ethoxyanol, and 0.81 g picolinic acid (5.8 mmol) were then mixed and reacted for 9 hr under nitrogen. After cooling, solid was precipitated and washed by small amount of water. After purification by silicon-gel column, 1.49 g yellow solid was obtained, with a yield of 60%.

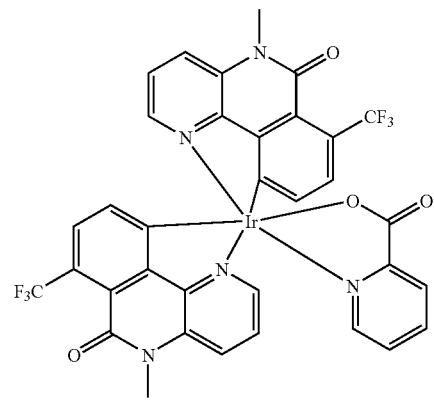

$^1$H NMR (CDCl$_3$, 400 MHz) spectrum data 9.28 (d, J=8.8 Hz, 1H), 8.73 (d, J=4.8 Hz, 1H), 8.62 (d, J=3.3 Hz, 1H), 8.39 (d, J=7.7 Hz, 1H), 8.14 (d, J=7.7 Hz, 1H), 8.02 (t, J=6.0 Hz, 1H), 7.92 (t, J=7.8 Hz, 1H), 7.76-7.70 (m, 2H), 7.55-7.39 (m, 2H), 6.74 (d, J=7.7 Hz, 1H), 6.48 (d, J=7.7 Hz, 1H), 3.84 (s, 3H), 3.81 (s, 3H).

EXAMPLE 24

Preparation of (C6BNO)$_2$$_1$Ir(acac)

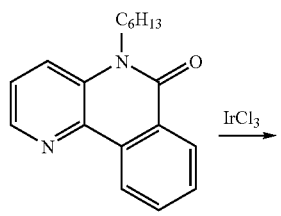

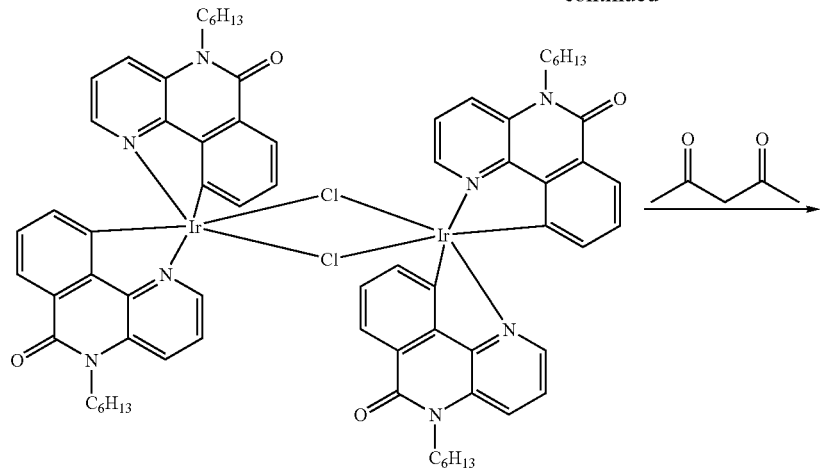

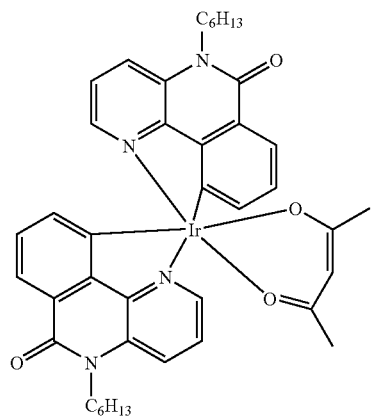

0.6 g Iridium (III) chloride hydrate (2 mmol), 1.24 g 5-hexyl-5H-benzo[c][1,5]naphthyridin-6-one (4.4 mmol), 24 mL 2-ethoxy ethanol, and 7 mL water were added and reacted for 24 hr under nitrogen. After cooling, filtration, and washing by small amount of methanol, a chlorine-bridged dimer complex was obtained. The complex, 1.06 g sodium carbonate (Na$_2$CO$_3$) (10 mmol), 25 mL 2-ethoxyanol, and 0.4 g acetylacetone (4 mmol) were then mixed and reacted for 9 hr under nitrogen. After cooling, solid was precipitated and washed by small amount of water. After purification by silicon-gel column, 0.73 g yellow solid was obtained, with a yield of 43%.

$^1$H NMR (CDCl$_3$, 400 MHz) spectrum data

δ 8.75 (d, J=5.4 Hz, 2H), 7.75-7.71 (m, 2H), 7.65 (d, J=8.3 Hz, 2H), 7.60-7.55 (m, 2H), 7.01-6.97 (m, 2H), 6.47 (d, J=7.3 Hz, 2H), 5.30 (s, 1H), 4.41-4.33 (m, 4H), 1.84-1.26 (m, 16H), 0.99-0.92 (m, 6H).

EXAMPLE 25

Preparation of (C6BNO)$_2$Ir(pic)

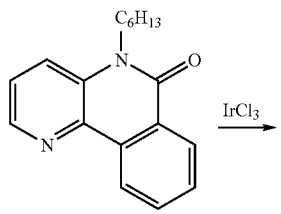

-continued

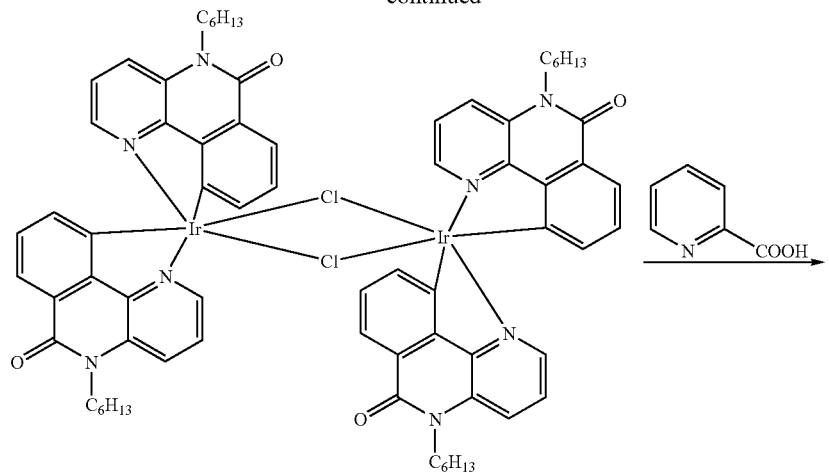

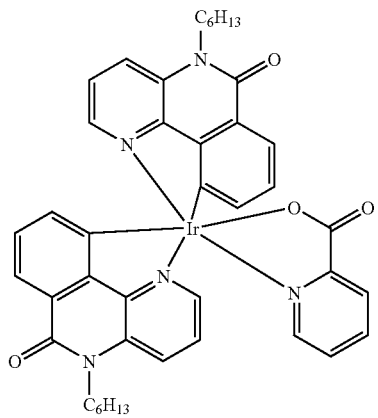

0.6 g Iridium (III) chloride hydrate (2 mmol), 1.24 g 5-hexyl-5H-benzo[c][1,5]naphthyridin-6-one (4.4 mmol), 24 mL 2-ethoxy ethanol, and 7 mL water were added and reacted for 24 hr under nitrogen. After cooling, filtration, and washing by small amount of methanol, a chlorine-bridged dimer complex was obtained. The complex, 1.06 g sodium carbonate ($Na_2CO_3$) (10 mmol), 25 mL 2-ethoxyanol, and 0.49 g picolinic acid (4 mmol) were then mixed and reacted for 9 hr under nitrogen. After cooling, solid was precipitated and washed by small amount of water. After purification by silicon-gel column, 0.67 g yellow solid was obtained, with a yield of 38%.

$^1$H NMR ($CDCl_3$, 400 MHz) spectrum data

δ8.68 (d, J=5.4 Hz, 1H), 8.36 (d, J=7.6 Hz, 1H), 7.96-7.81 (m, 4H), 7.63 (d, J=8.3 Hz, 2H), 7.46-7.42 (m, 1H), 7.39-7.34 (m, 2H), 7.26-7.20 (m, 1H), 7.15-7.05 (m, 2H), 6.70 (d, J=7.3 Hz, 1H), 6.46 (d, J=7.3 Hz, 1H), 4.48-4.22 (m, 4H), 1.83-1.78 (m, 4H), 1.57-1.27 (m, 12H), 0.94-0.92 (m, 6H).

EXAMPLE 26

The $(C1BNO)_2Ir(pic)$ complex of Example 20 and conventional $Ir(ppy)_3$ complex were utilized to prepare two electroluminescent devices, respectively, with the same doping concentration (6%). Their optoelectrical properties are shown in Table 1.

TABLE 1

| Host | Dopant | Driving voltage (V) | Luminescent efficiency (lm/W) | Max luminescence (cd/m$^2$) | CIE (x, y) |
|---|---|---|---|---|---|
| LT | $(C1BNO)_2Ir(pic)$ | 5.8 | 33.4 | 35,200 | (0.31, 0.58) |
| LT | $Ir(ppy)_3$ | 6.0 | 14.3 | 26,900 | (0.33, 0.58) |

The results indicate that the optoelectrical properties of the $(C1BNO)_2Ir(pic)$-containing electroluminescent device, such as driving voltage, luminescent efficiency, max luminescence, and CIE (green), are superior to the conventional $Ir(Ppy)_3$-containing electroluminescent device.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic metal complex having formula (I):

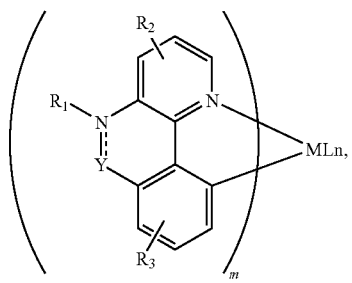
(I)

wherein $R_1$ comprises hydrogen, C1~C9 alkyl, C5~C8 cycloalkyl, or substituted or non-substituted aromatic groups;

$R_2$ and $R_3$ comprise hydrogen, fluorine, trifluoromethyl, C1~C9 alkyl, C5~C8 cycloalkyl, or substituted or non-substituted aromatic groups;

Y comprises C—R or carbonyl, wherein R comprises hydrogen, C1~C9 alkyl, C5~C8 cycloalkyl, or substituted or non-substituted aromatic groups;

L is a ligand;

M comprises iridium, platinum, ruthenium, gold, or palladium;

m is 1~3; and n is 0~2, wherein m+n is equal to the valence of M.

2. The organic metal complex as claimed in claim 1, wherein the aromatic group comprises heterocyclic rings containing oxygen, sulfur, or nitrogen.

3. The organic metal complex as claimed in claim 1, wherein the L comprises:

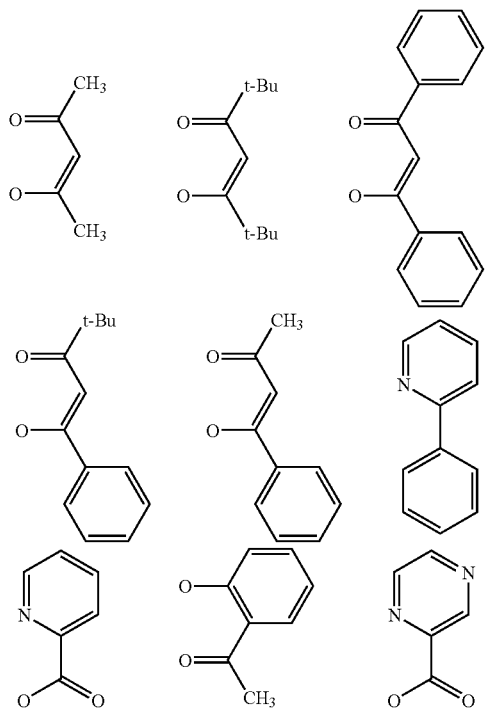

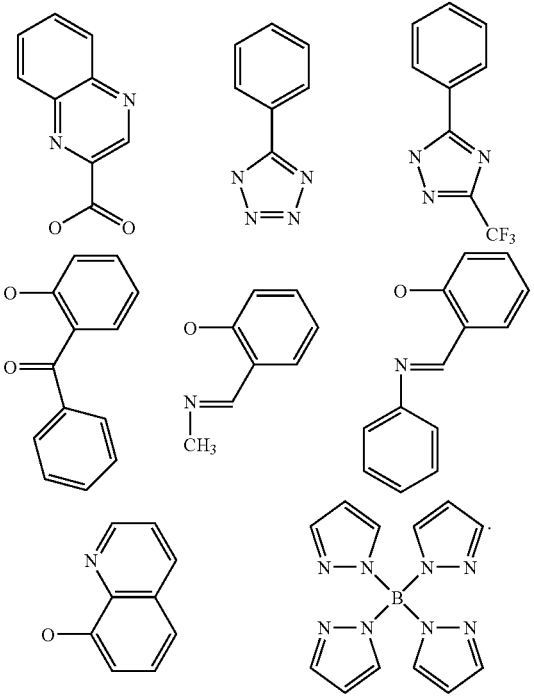

4. The organic metal complex as claimed in claim 1, wherein the organic metal complex is applied in electroluminescent devices.

5. The organic metal complex as claimed in claim 1, wherein the organic metal complex further has formula (II):

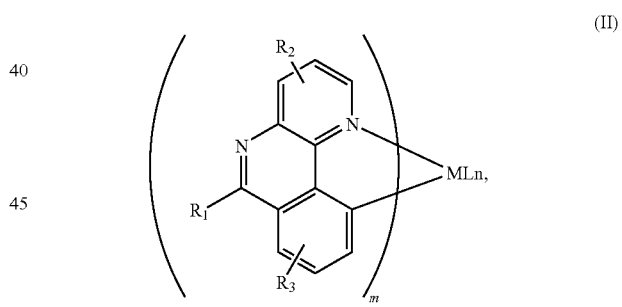
(II)

wherein $R_1$ comprises hydrogen, C1~C9 alkyl, C5~C8 cycloalkyl, or substituted or non-substituted aromatic groups;

$R_2$ and $R_3$ comprise hydrogen, fluorine, trifluoromethyl, C1~C9 alkyl, C5~C8 cycloalkyl, or substituted or non-substituted aromatic groups;

L is a ligand;

M comprises iridium, platinum, ruthenium, gold, or palladium;

m is 1~3; and n is 0~2, wherein m+n is equal to the valence of M.

6. The organic metal complex as claimed in claim 5, wherein the aromatic group comprises heterocyclic rings containing oxygen, sulfur, or nitrogen.

7. The organic metal complex as claimed in claim 5, wherein the L comprises:

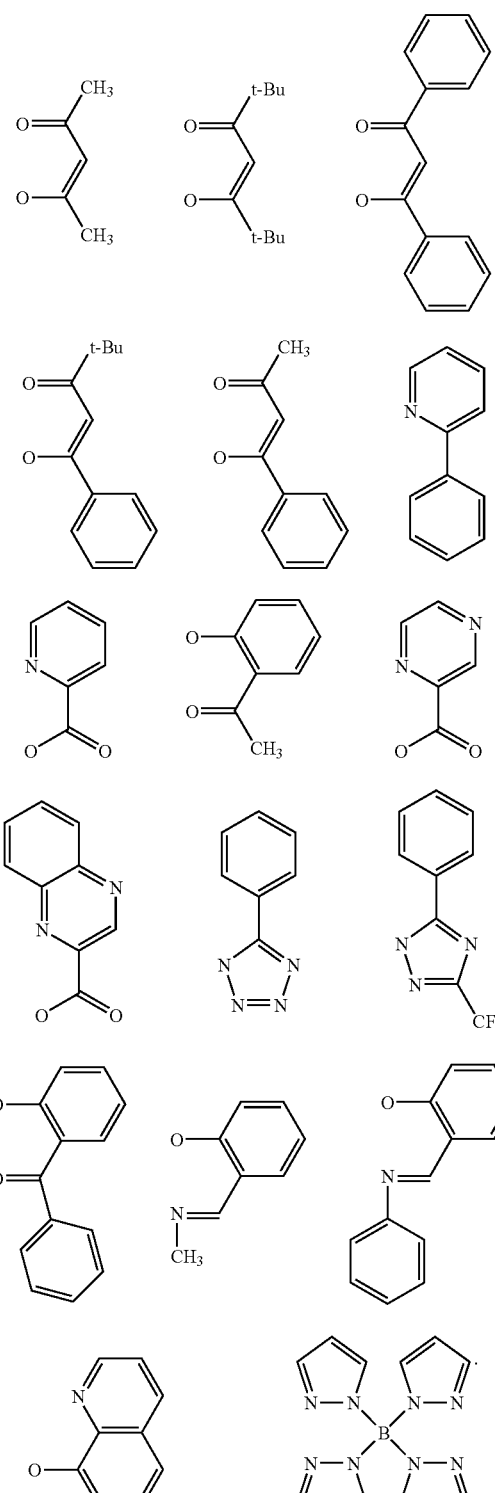

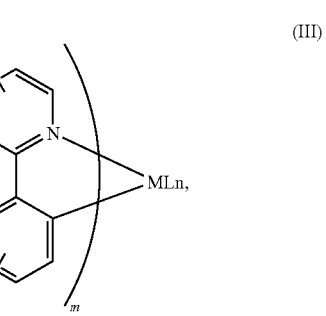

(III)

wherein $R_1$ comprises hydrogen, C1~C9 alkyl, C5~C8 cycloalkyl, or substituted or non-substituted aromatic groups;

$R_2$ and $R_3$ comprise hydrogen, fluorine, trifluoromethyl, C1~C9 alkyl, C5~C8 cycloalkyl, or substituted or non-substituted aromatic groups;

L is a ligand;

M comprises iridium, platinum, ruthenium, gold, or palladium;

m is 1~3; and n is 0~2, wherein m+n is equal to the valence of M.

10. The organic metal complex as claimed in claim 9, wherein the aromatic group comprises heterocyclic rings containing oxygen, sulfur, or nitrogen.

11. The organic metal complex as claimed in claim 9, wherein the L comprises:

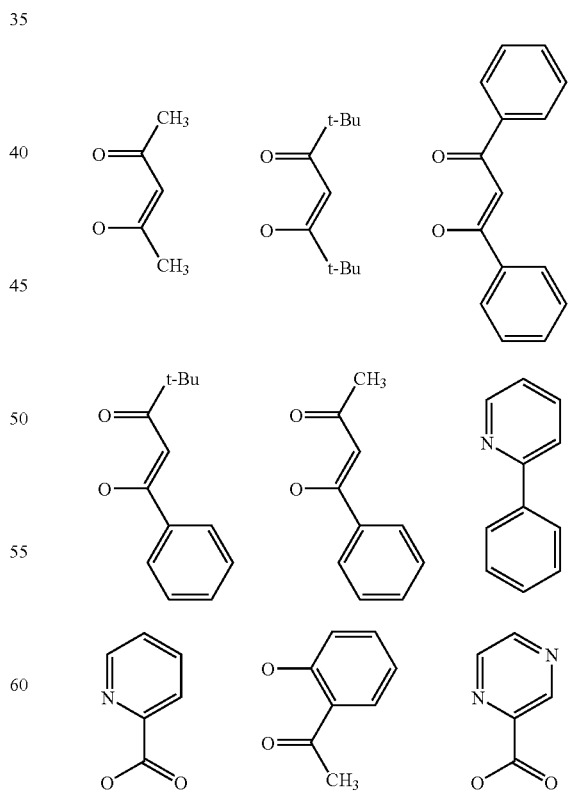

8. The organic metal complex as claimed in claim 5, wherein the organic metal complex is applied in electroluminescent devices.

9. The organic metal complex as claimed in claim 1, wherein the organic metal complex further has formula (III):

-continued

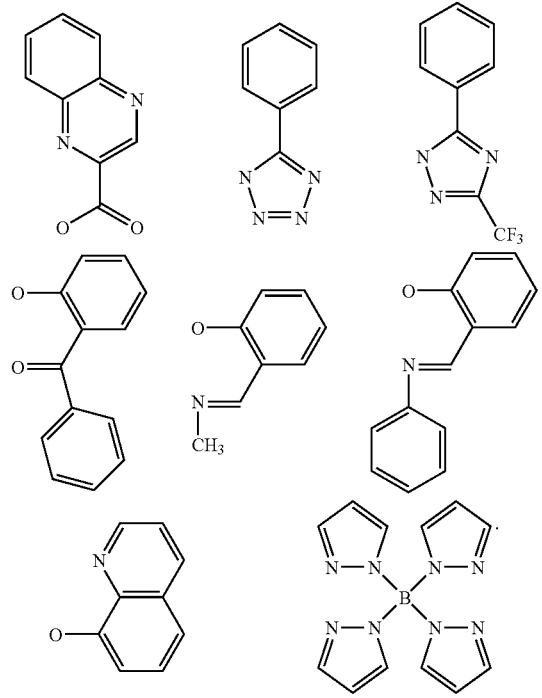

12. The organic metal complex as claimed in claim 9, wherein the organic metal complex is applied in electroluminescent devices.

13. The organic metal complex as claimed in claim 1, wherein the organic metal complex further has formula (IV):

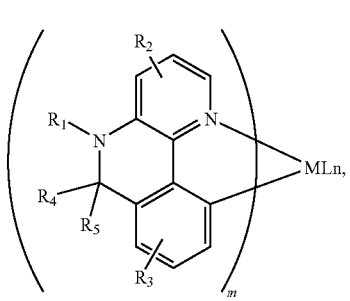

(IV)

wherein $R_1$, $R_4$, and $R_5$ comprise hydrogen, C1~C9 alkyl, C5~C8 cycloalkyl, or substituted or non-substituted aromatic groups;
  $R_2$ and $R_3$ comprise hydrogen, fluorine, trifluoromethyl, C1~C9 alkyl, C5~C8 cycloalkyl, or substituted or non-substituted aromatic groups;
  L is a ligand;
  M comprises iridium, platinum, ruthenium, gold, or palladium;
  m is 1~3; and
  n is 0~2, wherein m+n is equal to the valence of M.

14. The organic metal complex as claimed in claim 13, wherein the aromatic group comprises heterocyclic rings containing oxygen, sulfur, or nitrogen.

15. The organic metal complex as claimed in claim 13, wherein the L comprises:

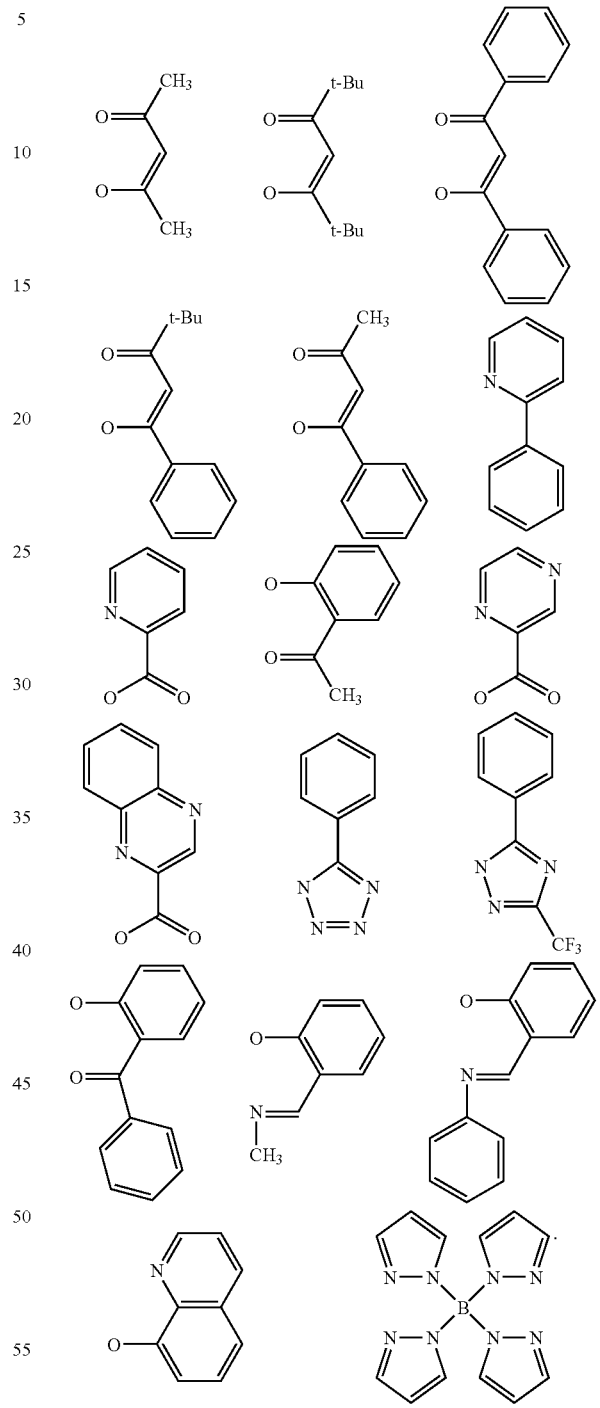

16. The organic metal complex as claimed in claim 13, wherein the organic metal complex is applied in electroluminescent devices.

* * * * *